(12) United States Patent
Chou et al.

(10) Patent No.: US 9,958,396 B2
(45) Date of Patent: May 1, 2018

(54) SENSING DEVICE, AND SENSING SYSTEM AND SENSING METHOD USING THE SAME

(71) Applicants: Academia Sinica, Taipei (TW); Centre National de la Recherche Scientifique, Paris (FR)

(72) Inventors: Chia-Fu Chou, Taipei (TW); Thierry Leichle, Toulouse (FR); Yii-Lih Lin, Taipei (TW); Pattamon Teerapanich, Toulouse (FR)

(73) Assignees: Academia Sinica, Taipei (TW); Centre National De La Recherche Scientifique, Paris (FR)

( * ) Notice: Subject to any disclaimer, the term of this patent is extended or adjusted under 35 U.S.C. 154(b) by 273 days.

(21) Appl. No.: 14/722,510

(22) Filed: May 27, 2015

(65) Prior Publication Data

US 2015/0346104 A1 Dec. 3, 2015

Related U.S. Application Data

(60) Provisional application No. 62/003,268, filed on May 27, 2014.

(51) Int. Cl.
*G01N 33/543* (2006.01)
*G01N 21/76* (2006.01)
(Continued)

(52) U.S. Cl.
CPC .......... *G01N 21/763* (2013.01); *B01L 3/5027* (2013.01); *G01N 21/6428* (2013.01);
(Continued)

(58) Field of Classification Search
None
See application file for complete search history.

(56) References Cited

U.S. PATENT DOCUMENTS 7,611,908 B2 * 11/2009 Miller ............... B01L 3/502761
422/417
7,858,041 B2 * 12/2010 Muraishi ................. B01L 3/021
422/511

(Continued)

FOREIGN PATENT DOCUMENTS

CN 1898016 A 1/2007
WO WO2004050247 A1 6/2004
(Continued)

*Primary Examiner* — Rebecca L Martinez
(74) *Attorney, Agent, or Firm* — Muncy, Geissler, Olds & Lowe, P.C.

(57) ABSTRACT

A sensing device applied to an analyte molecule of a liquid sample and a buffer flow has at least one first inlet, at least one second inlet, a micro-flow channel, and at least one immobilization element. The first inlet is for inputting the liquid sample. The second inlet is for inputting the buffer flow. The micro-flow channel communicates with the first inlet and the second inlet. The immobilization element is for immobilizing sensing molecules for the analyte molecules. The analyte sample flow and the buffer flow, in the reverse direction, in the micro-flow channel enable the association and disassociation kinetics to be obtained. The present invention further provides a sensing system and a sensing method using the sensing device.

15 Claims, 14 Drawing Sheets

(51) Int. Cl.
   *B01L 3/00*      (2006.01)
   *G01N 33/557*    (2006.01)
   *G01N 21/64*     (2006.01)
(52) U.S. Cl.
   CPC . *G01N 33/54366* (2013.01); *G01N 33/54373* (2013.01); *G01N 33/557* (2013.01); *B01L 2300/0636* (2013.01); *B01L 2300/0877* (2013.01); *G01N 21/6458* (2013.01); *G01N 2021/6439* (2013.01)

(56) References Cited

U.S. PATENT DOCUMENTS

| | | | |
|---|---|---|---|
| 8,178,046 B2 * | 5/2012 | Robotti | B01L 3/502715 257/431 |
| 2004/0005582 A1 | 1/2004 | Shipwash | |
| 2005/0161326 A1 | 7/2005 | Morita et al. | |
| 2010/0196205 A1 * | 8/2010 | Quinn | G01N 35/1095 422/82 |
| 2013/0130243 A1 | 5/2013 | Livache et al. | |

FOREIGN PATENT DOCUMENTS

| | | | |
|---|---|---|---|
| WO | WO2011134915 A1 | | 11/2011 |
| WO | WO2012118433 A1 | | 9/2012 |
| WO | WO2013/055281 | * | 4/2013 |
| WO | WO2014075016 A1 | | 5/2014 |

* cited by examiner

SENSING DEVICE, AND SENSING SYSTEM AND SENSING METHOD USING THE SAME

CROSS REFERENCE TO RELATED APPLICATIONS

This Non-provisional application claims priority to U.S. provisional patent application with Ser. No. 62/003,268 filed on May 27, 2014. This and all other extrinsic materials discussed herein are incorporated by reference in their entirety.

BACKGROUND OF THE INVENTION

Field of Invention

The present disclosure relates to a sensing device, a sensing system and a sensing method for biofunctionalized nanoslits combined with fluorescence microscopy for ultra-fast sensing kinetics studies of labeled molecules but with simple/low-cost setup.

Related Art

Kinetic monitoring of protein interactions offers fundamental insights of their cellular functions and is a vital key in developing potential diagnostic test and bio-therapeutic treatment. Surface plasmon resonance (SPR) and quartz crystal microbalance (QCM) are currently standard commercialized technology routinely used in the field of pharmaceutical and life sciences, offering a real-time detection of biomolecular interactions without label requirement. However, these techniques require high-cost dedicated sensor surface and integration of optical or mechanical components which in turn increases overall assay costs and complicate the instrument setup.

More specifically, surface plasmon resonance (SPR) requires high-cost sensor surface and sophisticated setup. SPR lacks spatial resolution and is expensive/complicated to implement, has low sensitivity (~nM), much (~1000×) higher amount of reagent consumption (10 μL), low multiplexing capability, high SPR chip cost (~$300/chip). QCM (Quartz crystal microbalance) has no spatial resolution and has low sensitivity. Moreover, QCM has no multiplexing capability and requires higher amount of reagent consumption and high chip cost (~$100/chip).

TIRFM (total internal reflection fluorescence microscopy) requires complicated apparatus, higher amount of reagent consumption. Integrated bioelectronics sensors involve complicated fabrication processes or electronics.

The typical platforms described above have low sensitivity (nM range) and are not suitable for small amount of sample consumption.

The time it takes to detect specific biomolecules in a sample is mainly limited by the detector sensitivity and the time it takes for the lowest number of molecules that can be detected to reach the sensor. While a wide range of very sensitive devices is now available (electrochemical sensors, optical sensors . . . ), when working with small sensing areas and low-concentration samples, the diffusion time is the main limiting factor for most microfluidic sensing platforms. Thus, overcoming diffusion is now mandatory in order to achieve ultra-fast detection. Technical solutions used in micro-total analysis systems, or microTAS, and microarray technologies consist in using convection and reciprocating flow in microchannels or nanochannels, in mixing the solution, and in locally increasing the concentration of biomolecules e.g. via dielectrophoresis. Though detection time can be reduced from several hours to several minutes using these methods, the main drawback of most of these methods is that they can be challenging to implement with highly complex manufacturing process.

SUMMARY OF THE INVENTION

To advance the state of the art, the present invention have witnessed remarkable research and development of novel micro- and nano-fluidic devices, allowing for single molecule analysis, cell sorting, DNA separation, and fast multiplexed protein detection. The combination of nanofluidics with advanced biosensor technology paves new roads for point-of-care clinical diagnostics particularly owing to their capability to integrate such devices into lab-on-a-chip as the dimensions scale down. Nanofluidic-based biosensors predominately reduce the consumption of costly biological reagents with enhanced speed of analysis thanks to the shorten diffusion distance between immobilized probe molecules and flowing analytes in confined channels.

To achieve the above, the present invention discloses a sensing device applied to an analyte molecule of a liquid sample and a buffer flow, comprising: at least one first inlet, at least one second inlet, a micro-flow channel, and at least one immobilization element. The first inlet is for inputting the liquid sample. The second inlet is for inputting the buffer flow. The micro-flow channel communicates with the first inlet and the second inlet. The immobilization element is for immobilizing a sensing molecule for the analyte molecule and the buffer flow in the micro-flow channel.

In one embodiment of the present invention, the sensing molecule is capable of generating an association reaction with the analyte molecule of the liquid sample, and generating a dissociation reaction with the analyte molecule and the buffer flow in reverse direction.

In one embodiment of the present invention, the micro-flow channel has an enough length so that the association reaction of the sensing molecule and the analyte molecule is observable.

In one embodiment of the present invention, the association reaction of the sensing molecule and the analyte molecule exhibits fluorescence.

In one embodiment of the present invention, the sensing molecule and the analyte molecule of the liquid sample generate the association reaction after the liquid sample flows into the micro-flow channel, then the sensing molecule and the analyte molecule generate the dissociation reaction after the buffer flow flows reversely into the micro-flow channel, namely, a reverse flow with respect to the association reaction.

In one embodiment of the present invention, the device further comprises a substrate and a cover. The substrate has a plurality of grooves corresponding to the first inlet, the second inlet and the micro-flow channel. The cover faces the grooves and combines with the substrate, wherein the cover and the grooves forms the first inlet, the second inlet and the micro-flow channel, The immobilization element is disposed on the groove corresponding to the micro-flow channel In one embodiment of the present invention, the material of the substrate comprises silicon, silicon dioxide, glass, and/or plastics, the material of the cover comprises polydimethylsiloxane, hard polydimethylsiloxane, polysilsesquioxane (PSQ), and/or plastics in bare form or coated on a glass slide, and the immobilization element is formed by surface treatment on the substrate with gold patch, glass or plastics.

In one embodiment of the present invention, the liquid sample flows along a first direction extending from the first inlet to the second inlet, and the range of the length of the micro-flow channel between the first inlet and the second inlet is between 100 μm~5 cm, the range of the average distance between the substrate and the cover is between 50 nm~10 μm, and the range of the length of the immobilization element on the first direction is between 1 μm to the whole micro-flow channel length.

In one embodiment of the present invention, the device further comprises a container communicating with the second inlet for storing the buffer flow.

In one embodiment of the present invention, the micro-flow channel comprises a plurality of nanoslits.

To achieve the above, the present invention discloses a sensing system comprising a device, a flow generator, a flow control unit, a capture unit and a computing unit. The flow generator connects to the first inlet and the second inlet. The flow control unit controls the flow generator to generate flow from the first inlet to the second inlet so as to drive the liquid sample or the buffer flow to flow into the micro-flow channel. The capture unit captures at least one image from the micro-flow channel. The computing unit generates a sensing result according to the image.

In one embodiment of the present invention, the flow generator includes one or more of the following: pressure pump or capillarity pump for pressure-driven flow, thermal gradient induced flow or electrokinetic pump for electroosmotic flow.

In one embodiment of the present invention, the capture unit captures time-lapse images from the micro-flow channel for association reaction and captures second set of time-lapse images from the micro-flow channel for disassociation reaction, and the computing unit utilizes association kinetics and dissociation kinetics to generate the sensing result according to the first time-lapse images and the second time-lapse images.

To achieve the above, the present invention discloses a sensing method comprising the following steps: driving the liquid sample into the micro-flow channel from the first inlet so as to associate the analyte molecule of the liquid sample with the sensing molecule; driving the buffer flow into the micro-flow channel from the second inlet so as to disassociate the analyte molecule from the sensing molecule; and generating a sensing result as a sensorgram according to the associating result and the disassociating result.

In one embodiment of the present invention, the generating step further comprises: obtaining an association kinetics information according to the associating result; obtaining a disassociation kinetics information according to the disassociating result; and obtaining the sensing result according to the association kinetics information and the disassociation kinetics information.

In one embodiment of the present invention, the generating step further comprises: analyzing a fluorescence intensity from the associating result to obtain an association kinetics information; analyzing another fluorescence intensity from the disassociating result to obtain a disassociation kinetics information; obtaining the sensing result according to the association kinetics information and the disassociation kinetics information.

In one embodiment of the present invention, the sensing method further comprises the following steps: driving a regenerating solution into the micro-flow channel; rinsing the micro-flow channel with the regenerating solution; and removing the regeneration solution from the micro-flow channel.

The present invention provides a sensing device, and a sensing system and a sensing method which are practically a biofunctionalized nanofluidic slits applied with classical fluorescence microscopy techniques, providing a simple, low-cost but still effective biosensing platform for kinetics studies. The sensing device includes a channel which depth is reduced to the sub-micrometer range, thus providing the following advantages of the present invention: (1) The drastic reduction of the diffusion length permits to operate in a reaction-limited regime with optimized target capture efficiency. Hence, all analyte molecules injected in the sensing device are analyzed, and the dissociation study can be simply implemented after completion of the association phase by reserving the fluid flow within the channel instead of injecting new buffer in the inlet, which results in a simplified operating protocol and reduced time of analysis; (2) a sampling volume reduction allows the device directly probing the immobilization element with conventional fluorescence microscopes without the need of using complicated and expensive setups, such as SPR, TIRFM, or QCM; (3) the signal to noise ratio is inversely proportional to the channel height: sub-micrometer channels thus offers signal to noise ratio of at least 100 on a large scale of dissociation constant $K_D$, from the pM to the sub-μM range, that concerns most molecules of interests.

Moreover, the sensing device, sensing system and the sensing method of the present invention enables large sampling area over a number of pixels ensuring much reduced statistical errors (higher precision) than non-spatially resolved sensing platforms. More importantly, Fluorescence microscopy offers a limit of detection under the pM with no effect of analyte mass, thus allowing the sensing device and the sensing method of very high-affinity interactions and small molecules.

The present invention solves the prior art problems by providing: (1) shortened kinetic assay time due to the reversed flow operation while higher level of detection sensitivity can be achieved with a very simple set-up, (2) efficient target capture for minute sample analysis, and (3) spatiotemporally resolved reaction/binding kinetics allowing for low statistical error.

BRIEF DESCRIPTION OF THE DRAWINGS

The present invention will become more fully understood from the subsequent detailed description and accompanying drawings, which are given by way of illustration only, and thus are not limitative of the present invention and wherein.

DETAILED DESCRIPTION OF THE INVENTION

The present invention will be apparent from the following detailed description, which proceeds with reference to the accompanying drawings, wherein the same references relate to the same elements.

The present invention provides a rapid and cost-effective nanofluidic based immuno-biosensor platform for real-time kinetic measurement of protein-protein binding, which is not for limit sense. With the combination of conventional bench top fluorescence detection system and reversed buffer flow, both association and dissociation kinetics can be accessed in one single experiment without rinsing buffer loading step, which is generally impractical for typical microfluidic based immunoassays.

In the present disclosure, a model based on finite element method is developed to quantify kinetic constants of two representative protein-ligand binding pairs: streptavidin-biotin and mouse IgG/anti-mouse IgG. The good agreement of extracted rate constants between the devices of the present disclosure and literatures versus SPR measurement indicates that this approach could be readily applicable to study protein interactions with sensitivity down to 1 pM.

The present invention has the advantages of multiplexing capability, very small volume of reagent needed and no wash required. Moreover, detection sensitivity can be down to ~1 pM with fast analysis time (in 30 min), advantageous compared to conventional ELISA method and current technology below. Further, the present invention achieves low sample volume consumption of 10.5 nL, which is translated into a mole detection limit of at least 10 zeptomole and high capture efficiency (no loss of target molecules).

The present invention offers essential techniques for the development of improved diagnostic tools and new therapy treatments against diseases. Over the last few decades, affinity based biosensors, exploiting the interaction between a free target analyte and an immobilized receptor on a solid surface, have been a key solution in characterizing biospecific interactions. This method reveals the affinity and kinetic information of various binding events particularly protein-ligands and nucleic acids.

Figure 1A:
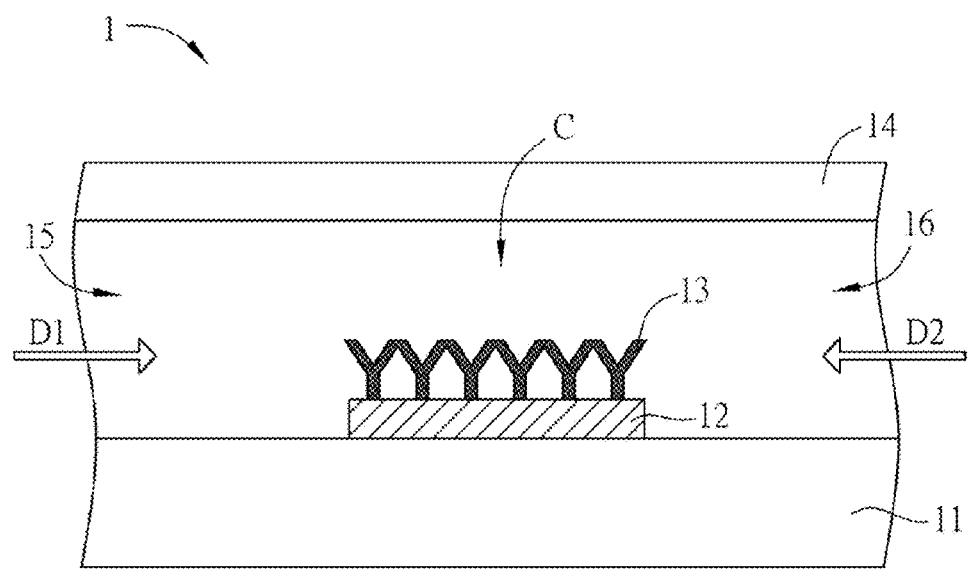
FIG. 1A is a schematic representation of a biofunctional nanoslit device used in protein kinetic study. Receptor probe molecules are immobilized on the immobilization element (sensing surface) located at the bottom of the nanochannel. Fluorescence labeled target molecules are introduced from the inlet by means of any kinds of introduced-flow to interact with the probe immobilized sensor. The kinetic reaction of protein-ligand binding is monitored in real-time using fluorescence microscopy.

Referring to FIG. 1A, in this embodiment, the present invention provides a sensing device 1 applied for detecting a liquid sample which includes a plurality of analyte molecules, especially biomolecules (e.g. protein, DNA . . . etc.). The sensing device 1 includes a substrate 11 which includes at least one immobilization element 12 (sensing area). A plurality of sensing molecules 13 are immobilized on the immobilization element 12.

Specifically speaking, the material of the substrate 11 includes silicon, silicon dioxide, glass, and/or plastics, and the immobilization element 12 is formed by conducting gold surface treatment, glass surface treatment or plastic surface treatment on part of the substrate 11, which is not for limit sense of the present invention. The amount of the immobilization element 12 is decided based on the practical experiment requirement. Otherwise, the sensing molecules 13 are chosen based on the species of the target analyte molecules.

The substrate 11 has a plurality of grooves (figure not shown) which are substantially micro- or nano-structures. The sensing device 1 also includes a cover 14 facing the grooves and combined with the substrate. The cover 14 and the grooves on the substrate 11 form at least one first inlet 15, at least one second inlet 16 and a micro-flow channel C. The immobilization element 12 is disposed on the groove corresponding to the micro-flow channel C. The amount of the first inlet 15, the second inlet 16 and the immobilization element 12 are not for limit set of the present invention. In this embodiment, the cover 14 and the grooves on the substrate 11 form a first inlet 15, a second inlet 16 and an immobilization element 12.

Referred to FIG. 1A, the liquid sample flows is introduced from the first inlet 15, which is practically conducted by a flow generator (not shown in figure), so as to associate the analyte molecule of the liquid sample with the sensing molecule. The liquid sample flows along a first direction D1 extending from the first inlet 15 to the second inlet 16. A buffer flow is introduced from the second inlet 16, which is also conducted by the flow generator mentioned above. The buffer flow flows a second direction D2 extending from the second inlet 16 to the first direction 15, that is, the liquid sample and the buffer flow flow along a completely counter direction of each other. Thus, the buffer flow is a reversed flow in contrast to the liquid sample flow.

In practical use, the above mentioned flow generator includes but not limited to pressure pump or capillarity pump for pressure-driven flow, thermal gradient induced flow or electrokinetic pump for electroosmotic flow.

Referring to FIG. 1A, the range of the length of the micro-flow channel C between the first inlet 15 and the second inlet 16 is between 100 µm~5 cm. In this embodiment, the length of the micro-flow channel C between the first inlet 15 and the second inlet 16 is of 500 µm. The range of the average distance between the substrate 11 and the cover 14 is between 50 nm~10 µm. In this embodiment, the average distance between the substrate 11 and the cover 14 is of 450 nm.

In addition, the range of the length of the immobilization element 12 on the first direction D1 is between 1 µm to the whole micro-flow channel C length. In this embodiment, the length of the immobilization element 12 on the first direction D1 is of 50 µm.

The present invention further provides a sensing system and a sensing method applied with the sensing device 1 mentioned above. The sensing system includes a sensing device 1 mentioned above, a flow generator connecting to the first inlet 15 and the second inlet 16, a flow control unit controlling the flow generator to press the first inlet 15 or the second inlet 16 so as to drive the liquid sample or the buffer flow to flow into the micro-flow channel C, a capture unit capturing at least one image from the micro-flow channel C, and a computing unit generating a sensing result according to the image. The techniques and the implementation details of the sensing system have been disclosed by the above-mentioned description and referred by the experiment example mentioned below, hence, the details are not repeated here.

The sensing method includes the following steps: driving the liquid sample into the micro-flow channel from the first inlet so as to associate the analyte molecule of the liquid sample with the sensing molecule; driving the buffer flow into the micro-flow channel from the second inlet so as to disassociate the analyte molecule from the sensing molecule; and generating a sensing result according to the associating result and the disassociating result. The techniques and the implementation details of the sensing method have been disclosed by the above-mentioned description and referred by the experiment example mentioned below, hence, the details are not repeated here.

Figure 1B:
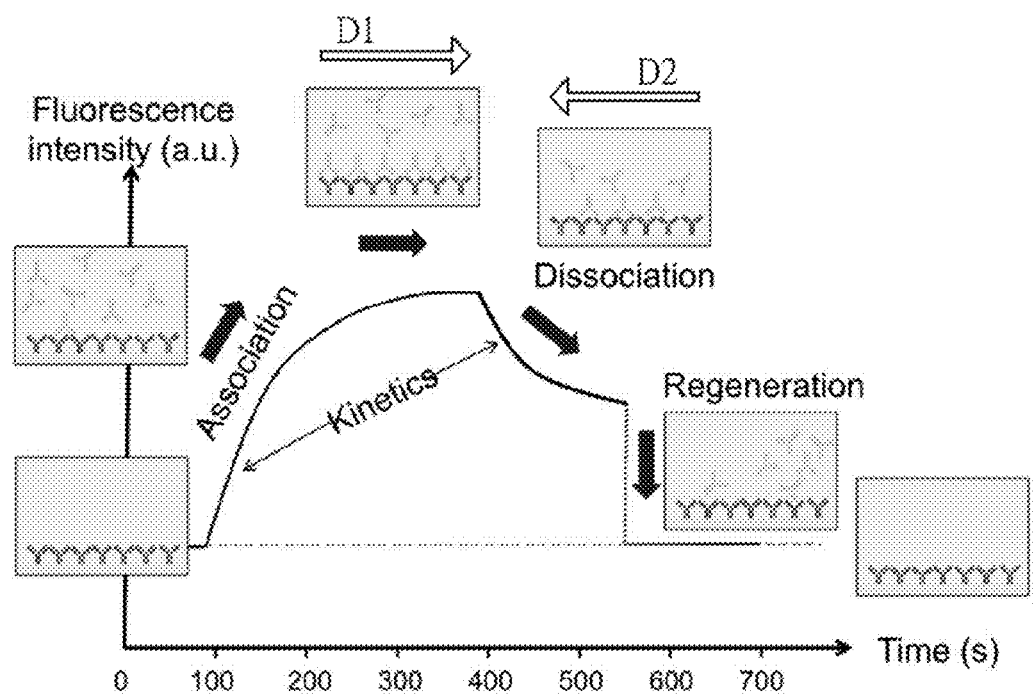
FIG. 1B is a typical sensorgram of kinetic analysis performed in the nanofluidic device of FIG. 1. During association phase, the flowing analyte binds to the immobilized receptor molecules on the sensor surface, resulting in an increase in fluorescence intensity. After reaching equilibrium where the rate of association is equal to the rate of dissociation, a buffer solution is introduced from a reversed direction in the channel and the receptor-analyte complex is allowed to dissociate. In regeneration step, a regeneration solution is used for a short period of time to disrupt binding and regenerate the free receptor for the next measurement cycle.

Referring to FIG. 1B, the devices of the present disclosure are capable of generating full kinetic sensorgram including both association and dissociation phases in one single-experiment with a single injection via reversed buffer flow. In addition, a model based on finite element method was developed using COMSOL multiphysics software to predict the binding responses of immunoreaction inside nanoslits. Finally, the on/off rate constants of protein-ligand interactions were determined and the extracted values were validated with the one from literatures and analogous SPR measurements.

The following and accompanying figures take a number of experiments for examples to describe the main details of the method for sensing target analyte molecules in accordance with the embodiments of the present invention.

Experiments

Materials and Reagents

Biotinylated tri(ethylene glycol) undecane thiol (BAT) (HS—(CH)n-OEG-biotin) was purchased from Nanoscience Instruments (USA). 11-mercapto-1-undecanol (MUD) (HS—$(CH_2)_{11}$—OH), bovine serum albumin (BSA) were purchased from Sigma-Aldrich (France). Tween-20 was purchased from ACROS Organics (France). Biotinylated anti-mouse IgG and Alexa Fluor 647 conjugated monoclonal mouse anti-rabbit IgG were purchased from Jackson ImmunoResearch (UK). Alexa Fluor 488 conjugated streptavidin and Alexa Fluor 660 conjugated goat anti-rabbit were purchased from Invitrogen, Inc. All proteins were diluted in phosphate buffer saline (PBS) (10 mM PBS, 0.138 M NaCl, 0.0027 M KCl, pH 7.4) purchased from Sigma-Aldrich (France). Five product compositions for hard-PDMS preparation, vinyl PDMS copolymer, vinyl modified silica Q resin, platinum-divinyltetramethyldisiloxane, hydrosilane prepolymer and 2,4,6,8-tetramethyl-tetravinylcyclotetrasiloxane, were purchased from abcr GmbH & Co. Kg (Germany) and Sigma-Aldrich (France). All other chemicals were of analytical grade and used without further purification. The SPR measurements were performed on a BIACORE 3000 apparatus (Biacore AB, Uppsala, Sweden) and the Au-SIA kit was purchased from Biacore AB. Pico plasma cleaner from Diener electronic GmbH+Co. Kg (Germany) was used for surface activation.

Nanofluidic Chip Design and Fabrication

Figure 8:
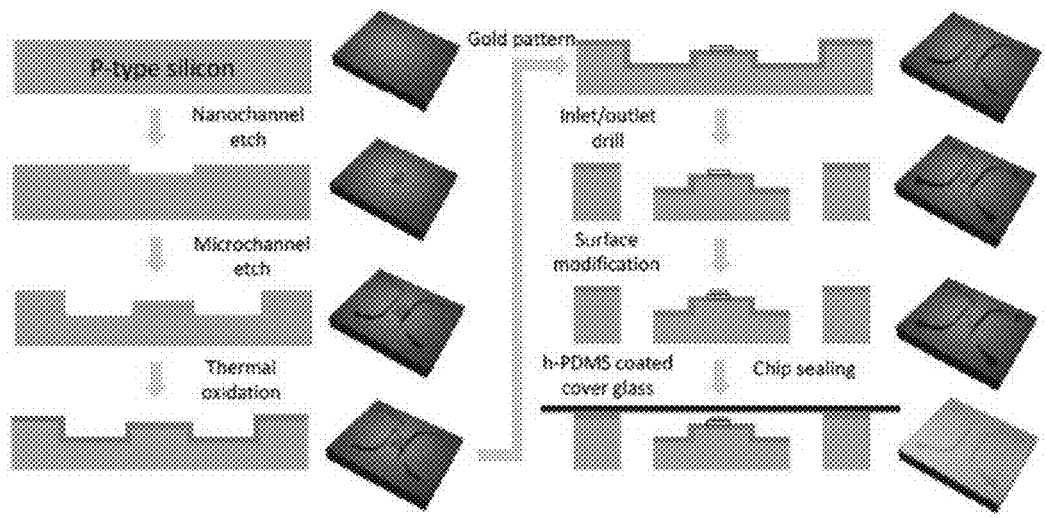
FIG. 8 is a schematic diagram of biofunctional nanoslit fabrication and chip encapsulation procedure.

Referring to FIG. 8, a schematic diagram of biofunctional nanoslit fabrication and chip encapsulation process is shown. Nanofluidic chip was designed in a CleWin4 Layout Editor (Wieweb software, Netherlands) and printed on a chrome mask. The device consists of parallel nanochannels, 50 µm in width and 450 nm in depth connected by two microchannels, 400 µm in width and 5 µm in depth. The chip was fabricated on 100 mm P-type silicon wafer with standard photolithography. The photolithography was used to define the width and the length of nano- and microchannels.

First, 2.6 µm thick positive ECI photoresist was spin-coated on hexamethyldisilazane (HMDS) pre-treated silicon wafer, UV exposed and developed, followed by reactive ion etching (RIE) to achieve 450 nm deep nanochannels. The similar processes were performed by aligning a photoresist pattern of microchannels on the etched wafer, creating nanoslit and microchannel structures on the same wafer. The wafer was then thermally oxidized creating a 200 nm thin oxide layer to ease liquid filling and chip bonding. To selectively immobilize protein receptors at the bottom of nanochannels, a 5/100 nm Cr/Au film was evaporated onto the clean etched silicon wafer and lifted-off. Finally, the inlet/outlet holes were drilled from the back side of the wafer by a sandblasting machine and the wafer was diced into the individual silicon chips.

Pre-Surface Immobilization Protocol and Chip Assembly

Pre-surface immobilization protocol used in this study is based on self-assembled monolayer (SAM) of mixed thiols on the gold surface. This method offers a long-term stability, reproducibility and good orientation of the immobilized protein as well as a desired surface probe density by tuning the mixture ratio in loading solutions. The formation of well-organized monolayer requires long incubation period (~12-48 hours). As a result, open-top immobilization protocol was chosen to introduce a biotin functional group on the patterned gold patches prior to chip encapsulation. Briefly, the piranha cleaned chips were incubated overnight with a mixture of 0.1:9.9 by mole (1% BAT for streptavidin-biotin binding model) or 1:9 by mole (10% BAT for mouse IgG/anti-mouse IgG binding model) of biotin-terminated thiol and 11-mercapto-1-undecanol with a 0.5 mM total concentration in absolute ethanol, sealed under nitrogen. The substrates were then removed, washed thoroughly in ethanol, followed by deionized water to remove excess thiol compounds and dried with nitrogen.

For chip encapsulation, a thin layer of hard- was spin-coated at 3000 rpm for 30 s onto piranha cleaned cover glass followed by 1 hour curing at 75° C. The hard-PDMS (h-PDMS) coated cover glass was activated by exposure to plasma oxygen (120 s, 35 W, 0.5 mbar $O_2$) and then immediately placed in contact on biotin-modified nanoslit to achieve a covalent bond via siloxane linkage. The chip was then baked at 75° C. for 5 min and a 10 µl of blocking buffer solution (1% BSA in 1×PBS buffer+0.02% Tween-20) was loaded into the fluidic chip by capillary forces and incubated for 3 hours to prevent protein non-specific binding on silicon dioxide and h-PDMS areas.

Figure 9:
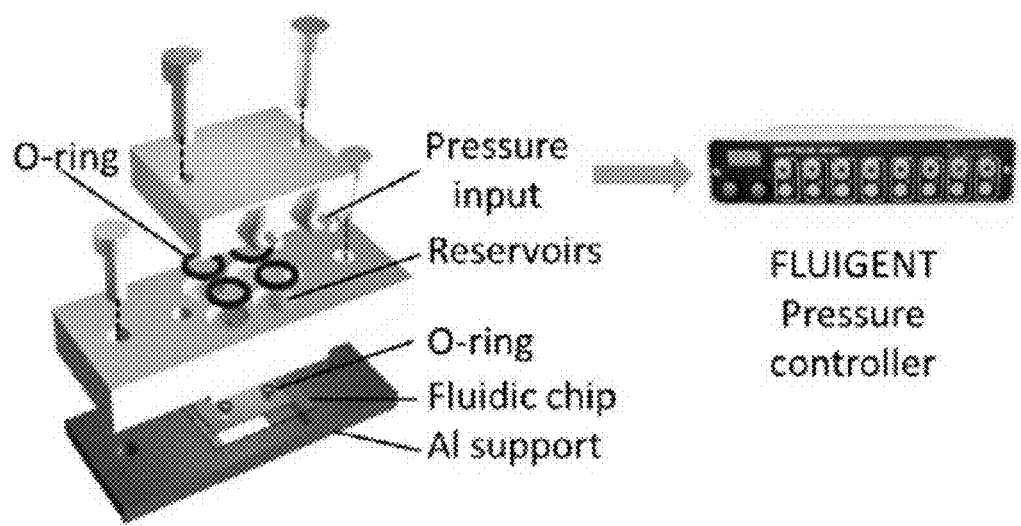
FIG. 9 is a schematic presentation of chip assembly based on pressure-driven flow. The fluidic chip is placed upside-down in a gasket support made in aluminum, wherein a Teflon piece consisting of four reservoirs is located on top of the fluidic chip, and a pressure input made of Teflon is used to seal the entire system and connect to a pressure controller with the aid of O-ring and Teflon screws at each interface to prevent leakage.

Referring to FIG. 9, a schematic presentation of chip assembly based on pressure-driven flow is shown. The fluidic chip is placed upside-down in a gasket support made in aluminum. A Teflon piece consisting of four reservoirs is located on top of the fluidic chip. A pressure input made of Teflon is used to seal the entire system and connect to a pressure controller with the aid of O-ring and Teflon screws at each interface to prevent leakage.

The chip was finally mounted on the fluidic support and the reservoirs were connected with a pressure controller system (MFCS-8C Fluigent, France) to induce liquid flow. A rigid and compact support was designed to assemble the chip providing the link to the external fluidic components.

Fluorescence Data Acquisition and Analysis

Protein binding kinetics inside nanoslits were imaged using an inverted microscope (Olympus IX 70) with an iXonEM+885 EMCCD (1004×1002 active pixels, 8×8 µm² pixel size) from ANDOR equipped with a white light source (Lumencore SOLA light Engine®, USA). Fluorescence images were acquired with a LCPlanF1 20×/0.40 Ph1 objective (Olympus Optical, Japan) and appropriate filter sets (U-MWIB3 from Olympus and U-M41008 from Chroma). An exposure time of 1 s, using an external shutter (Lambda SC, Shutter Instrument) triggered by the camera, was employed to avoid photobleaching and all measurements were carried out at room temperature.

Figure 2:
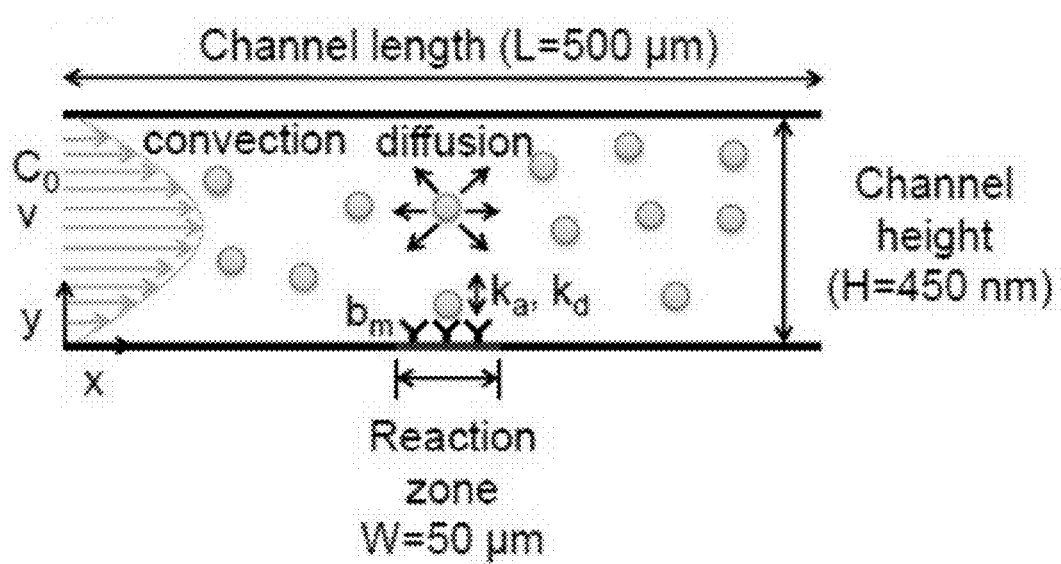
FIG. 2 is 2-D model used in finite element simulation of heterogeneous immunoreaction in a nanofluidic channel with channel length (L) of 500 μm and channel height (H) of 450 nm, containing a sensing area of 50 μm in length (W) at the bottom of the channel. The analyte with concentration of $C_0$ is introduced to the channel from the left inlet with fluid flow velocity (v). Analyte molecules are transported along the channel length in x direction by the convective flow. They are allowed to diffuse freely in all directions and captured by probe molecules immobilized on the reaction zone with surface probe density ($b_m$). Kinetics of biospecific interactions are defined by their association ($k_a$) and dissociation rates ($k_d$).

The fabricated device has several identical nanochannels in parallel. Therefore, only one nanochannel is considered as a representative immunoassay of our system. FIG. 2 shows a schematic of the heterogeneous immunoreaction in a nanofludic channel. In this work, the dimensions of nanochannel are 450 nm in depth (H) and 500 µm in length (L). A 50 µm length sensor patch immobilizing capture ligands are located at the bottom center of the nanochannel. Inlet and outlet are defined as the opening of nanochannel at the beginning and at the end of the geometry, excluded the mass transport in microchannel since there is no effect on the flow velocity profile inside nanochannel. The analyte molecules are introduced from the left inlet to the right outlet with a flow velocity (v). They are allowed to diffuse with a diffusion coefficient (D) and captured by the probe immobilized sensor with on/off rate constants ($k_a$, $k_d$). For the ranges of simulation parameters, bulk analyte concentration ($C_0$) of 0.46-100 nM and flow velocity (v) of 155-200 µm/s determined by bead analysis and theoretical calculation were used. The effective surface probe density ($b_m$) was obtained from analogous SPR measurements in a range of $1\times10^{-9}$ to $4\times10^{-8}$ mol/m². The diffusion coefficients (D) were $7.4\times10^{-11}$ m²/s for streptavidin molecule (53 kDa) and $1\times10^{-11}$ m²/s for mouse IgG (150 kDa). The ranges of association rate constant $k_a$ and dissociation rate constant $k_d$ for streptavidin-biotin binding interactions were $1.5\times10^5$ to $1.4\times10^6$ M$^{-1}$s$^{-1}$ and $1.0\times10^{-7}$ to $8.8\times10^{-6}$ s$^{-1}$, respectively.

The ranges of $k_a$ and $k_d$ for mouse IgG/anti-mouse IgG binding interactions were $6.0 \times 10^5$ to $9.0 \times 10^5$ M$^{-1}$ s$^{-1}$ and $5.0 \times 10^{-4}$ to $7.0 \times 10^{-4}$ s$^{-1}$, respectively. These ranges of kinetic parameters were obtained from literature values.

Device Fabrication and Fluidic Handling

The devices consist of microfluidic channels linked by parallel identical nanochannels fabricated in silicon wafer using simple and straight-forward methods including conventional photolithography and reactive ion etching. A thin oxide layer formed on the silicon substrate promotes facile chip encapsulation and aqueous solution filling. Comparable to SPR measurement, a gold surface was chosen for surface immobilization of bioreceptor probe that is selective to target analyte molecules. PDMS elastomer is commonly used to fabricate microfluidic devices due to its desirable properties. However, PDMS is impractical for the fabrication of nanofluidic devices with high aspect ratio. A hard-PDMS, owing similar property and functionality as PDMS but more cross-linked polymer or harder, is an alternative material which offers 4.5 times Young's modulus higher than that of a standard PDMS. Due to its hardness, pressure-induced deformation in h-PDMS can be dramatically reduced, leading to successful fluidic chip encapsulation particularly in nanoscale devices. As a result, a h-PDMS coated cover glass was employed in place of a regular PDMS to avoid channel collapsing upon device sealing in this study.

Positive pressure generated by a Fluigent system was utilized throughout our experiments to introduce the liquid or biological samples into nanoslits. A pressure driven-flow method was chosen since a precise flow control and facile fluid handling can be achieved which is indispensable for immunoassay. Moreover, it is simple to implement and it is insensitive to surface contaminants, ionic strength and pH compared to electrokinetic flow. Basically, the nanofluidic chip is composed of two microchannels used to introduce liquid and connect to the external fluid apparatus (tubing and pressure generator) while parallel straight nanochannels were used to conduct the binding kinetics of protein interaction. There are two inlets and two outlets situated at the end of microchannels.

Figure 3:
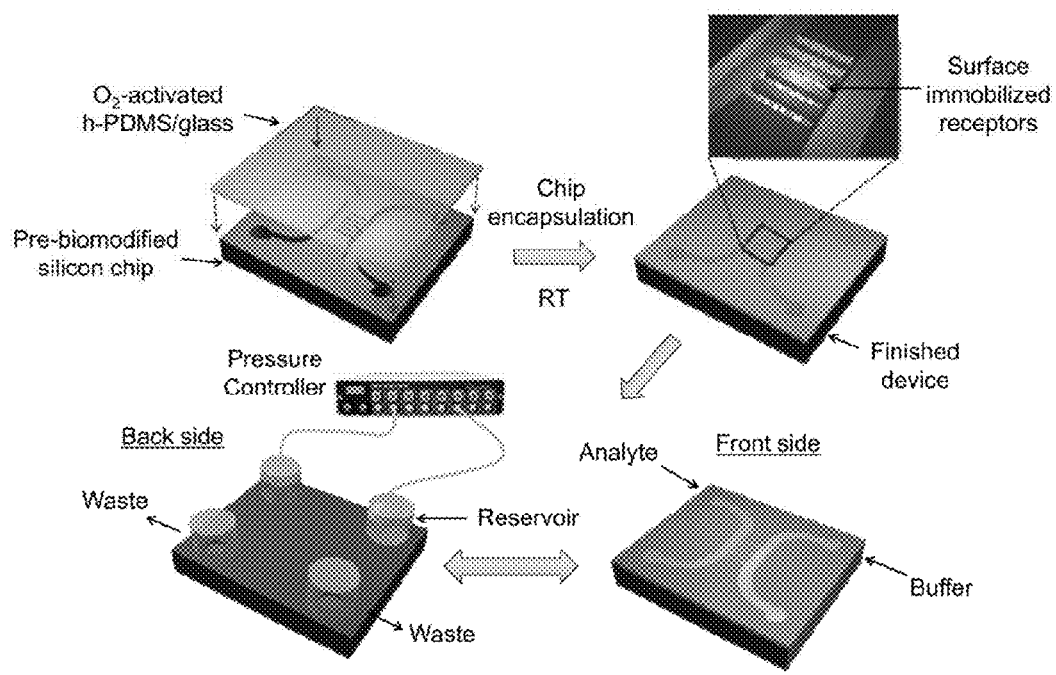
FIG. 3 is diagrams illustrating a biofunctional nanoslit encapsulation procedure and fluidic connections. The analyte solution is introduced from one inlet while another inlet is used for buffer injection, allowing the study of association and dissociation phases of immunoreactions in one single-experiment via reversed buffer flow manner.

Referring to FIG. 3, in kinetic experiments, the first inlet was used to introduce the liquid sample (target analyte solution) and the buffer solution was injected from the second inlet. Based on this configuration, the pressure can be applied on both inlets either separately or simultaneously. As a result, a full kinetic sensorgram (association and dissociation curves) can be achieved using a reversed flow manner in order to switch from analyte to buffer solution without removing the fluidic setup which is commonly impractical in case of classical microfluidic setup.

Model I: Streptavidin-Biotin Binding Model

The bio-functionality and compatibility of the open-top surface modification in combination with the asymmetric bonding technique were investigated using streptavidin-biotin reaction based on pressure-driven flow inside nanofluidic device. To study this specific biomolecular interaction, a 100 nM solution of Alexa Fluor 488 conjugated streptavidin (ST-AF 488) was delivered into 10% biotinylated thiol modified channel loaded with a blocking buffer (1% BSA in 10 mM PBS buffer+0.02% Tween-20, pH 4) at a constant flow velocity of 155 μm/s for 15 min. After rinsing with buffer (10 mM PBS buffer+0.05% Tween-20, pH 7.4) to remove excess streptavidin molecules from the channel and any non-specific adsorption on the surface, the fluorescence images were recorded. A significant increase in fluorescence intensity on the sensor patches containing pre-immobilized biotin molecules was observed, while the adjacent area on the channel wall remains relatively low fluorescence intensities. A control experiment (no biotin) was also conducted on hydroxyl-terminated thiol (a spacer) modified sensor surfaces. No significant non-specific physical adsorption was observed after washing step (data not shown). This indicates the specific recognition between pre-immobilized biotin and flowing streptavidin target molecules. These results confirm that pre-modified probe molecules maintained their bio-reactivity towards specific target after chip encapsulation procedure, providing a sensing capability with high signal-to-noise ratio and diminished non-specific adsorption.

Figure 4:
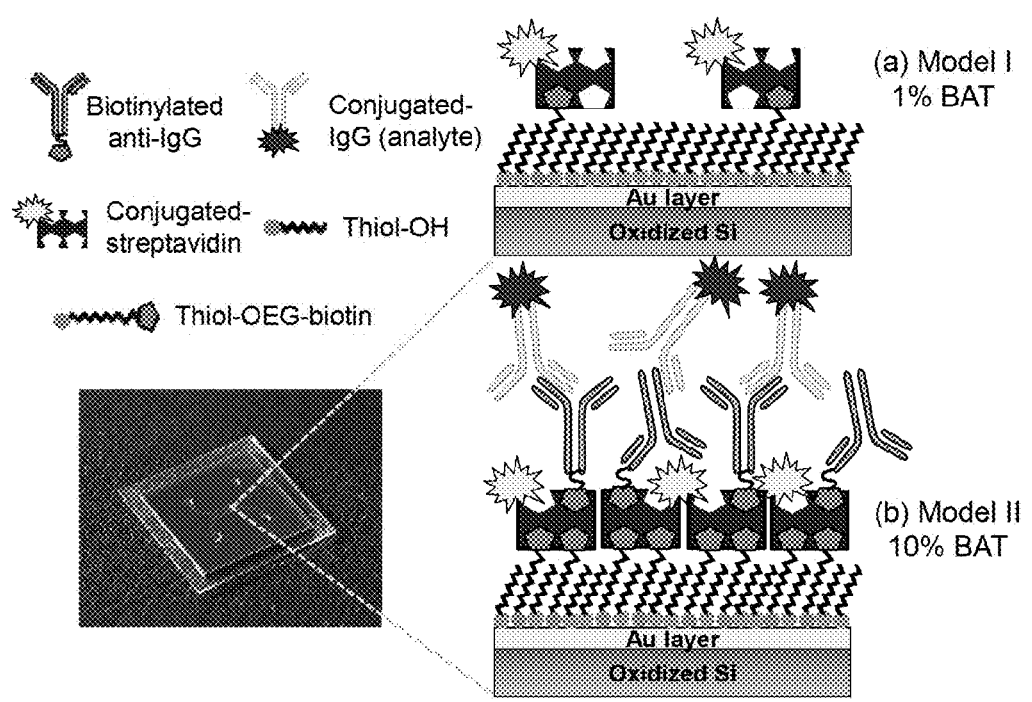
FIG. 4 shows schematic illustrations (not to scale) of two surface functionalization architectures on gold sensors used for protein kinetic study in nanoslits. (a) Model I shows streptavidin-biotin interaction on 1% biotinylated thiol modified surface; (b) Model II shows mouse anti-rabbit IgG/anti-mouse IgG interaction via biotin-streptavidin linkage on 10% biotinylated thiol modified surface. Hydroxyl-terminated thiol compound acts as a spacer to reduce non-specific adsorption of proteins on gold surfaces. The photograph of fabricated nanoslit device is also demonstrated.

The interaction between immobilized biotin molecules and flowing fluorescently labeled streptavidin molecules was studied in the biotinylated thiol modified nanochannel. The surface immobilization construction on sensing areas is shown in FIG. 4A. As streptavidin-biotin interaction naturally possesses extremely high affinity ($K_d = 10^{-13}$M), a 1% (by mole) biotin content was chosen to modify the gold surface in order to minimize the problem of analyte transport limitation and steric hindrance particularly at high surface probe density and to avoid using a high injection flow rate which in turn enhances reagent consumption. The evaluation of two key dimensionless numbers, Peclet and Damköhler numbers, plays a crucial role in a high performance biosensor design. It is essential to ensure that the kinetic information obtained from immunoreaction is a true representation of binding events inside our nanofluidic device since binding constants can be directly influenced by mass transfer of target analyte. The Peclet number ($P_e$) for our experimental conditions regarding to the applied flow velocity and reaction channel height were calculated as close to unity ($P_e = U_m H/D$, where D is the diffusion coefficient of biomolecules), meaning that the time for the analyte to diffuse across the entire height of the channel will be equal to the time for the analyte to be transported over the sensor via convection. Theoretically, all analyte molecules in the channel should have the possibility to interact with the probe on the sensor surface, and the system will approach the limit of full collection where $P_e < 0.5$. This elucidates a high sensing performance with enhanced analyte binding efficiency and short response time of our nanoslit system. According to the calculated Damköhler number using an effective probe density obtained from analogous SPR measurement ($b_m = 4 \times 10^{-8}$ mol/m$^2$), kinetic reactions fall into a reaction-limited regime and not diffusion-limited.

Kinetic measurements were conducted after biotin modification on sensor surfaces. ST-AF 488 solutions ranging in concentration from 10 nM to 100 nM were introduced continuously at a constant flow velocity of 155 μm/s and allowed to bind with biotin immobilized on sensor surfaces. The fluorescence images were recorded in real-time to monitor the association process of this specific binding event. Due to very high binding affinity and exceptionally long dissociation time of streptavidin-biotin recognition system, four different devices were employed to measure the binding constants of streptavidin at each concentration.

Figure 5A:
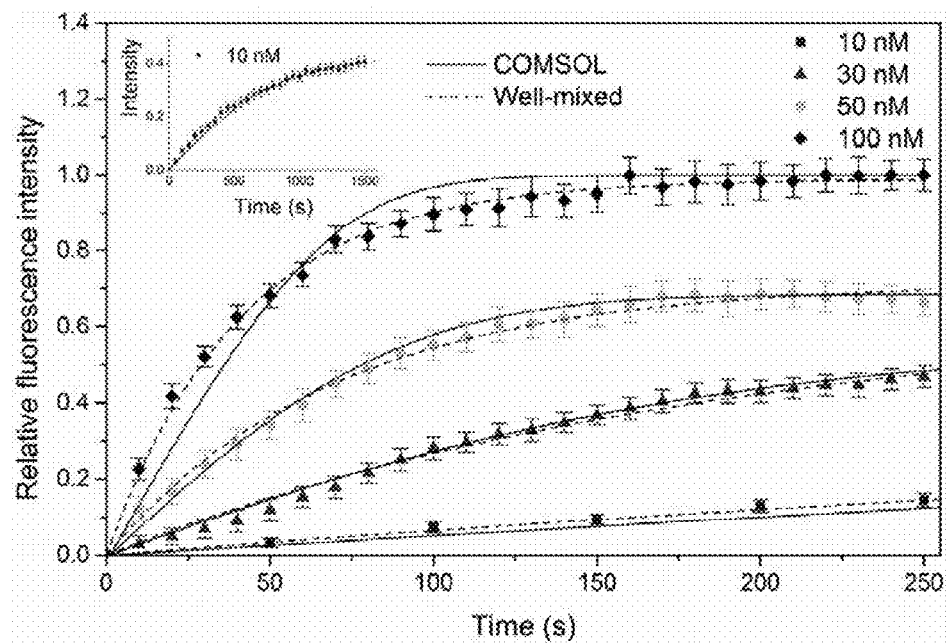
FIG. 5A shows real-time sensor responses of streptavidin-biotin interaction measured in biofunctional nanoslits. Kinetic curve obtained from each concentration is attributed to the measurement from a different nanofluidic device (the error bars: standard errors). The sensor responses were normalized to the relative fluorescence intensity and fitted with the computation model based on finite element method and well-mixed model assuming a simple Langmuir 1:1 interaction. The black (-) and (- - -) lines represent the predicted curves from the best fit of finite element simulation and well-mixed model, respectively. Due to a long response time, a binding curve of a lowest concentration of streptavidin (10 nM) is also plotted separately in the inset figure.
Figure 10:
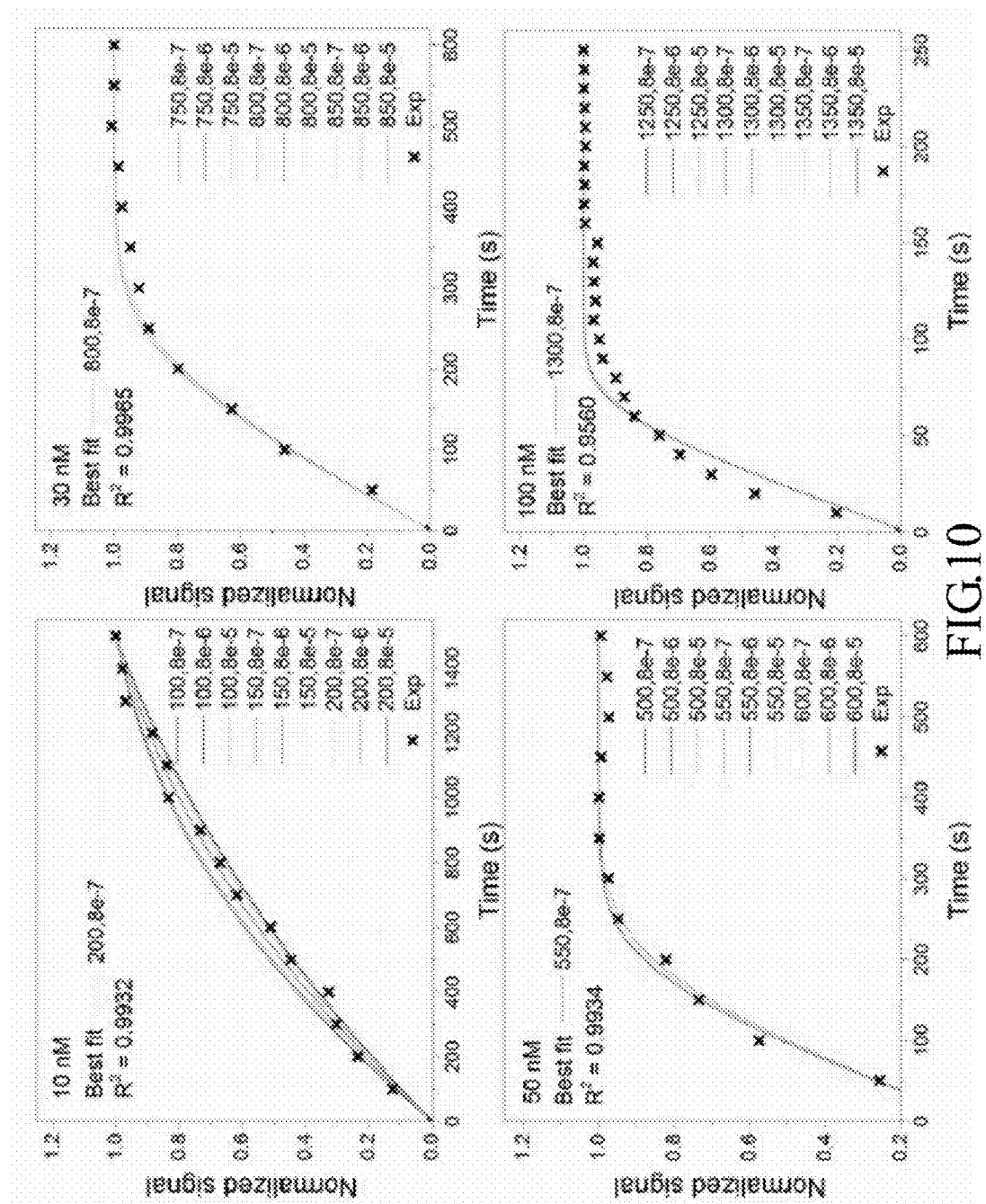
FIG. 10 shows extraction of kinetic constants for streptavidin-biotin interaction. The experimental data of various streptavidin concentrations (10, 30, 50 and 100 nM) (x) are plotted with the simulated curves (-) obtained from finite element computation model at different association and dissociation rate constants. The surface probe density and flow velocity were kept the same in all cases. The extracted rate constants were determined from the best fit of the predicted binding curves to the experimental data by means of coefficient of determination.

The fluorescence intensities were normalized and fitted with the simulated data attained from finite element model. The relative sensor responses of streptavidin-biotin binding at various concentrations fitted with a simulation model are shown in FIG. 5A. It was observed that the experimental data of streptavidin binding at low concentration (10-50 nM) fitted the simulation data well with R-square in a range of 0.99. Nevertheless, high concentration of streptavidin (100 nM) shows a relatively poor fit with the simulation results (R-square=0.95). This might be due to several reasons pronounced at high analyte concentration including steric hindrance, heterogeneity of the surface, non-specific binding, deviation from 1:1 interaction model etc. To determine the binding affinity based on computational model, the association and dissociation rate constants at each concentration were extracted from the best fit of the predicted binding curves to the experimental data (FIG. 10). The average association rate constant ($k_a$) was determined to be $7.1 \times 10^5$ $M^{-1}s^{-1}$ and dissociation rate constant ($k_d$) of $0.80 \times 10^{-6}$ $s^{-1}$ was observed from the best fit for all concentrations. Additionally, a lower off-rate was also applied in the simulation model, but there was no change in sensor responses. As a result, dissociation constant ($K_D$) for streptavidin-biotin interaction can be estimated as $Kd \leq 1.2 \times 10^{-12}$ M.

Figure 5B:
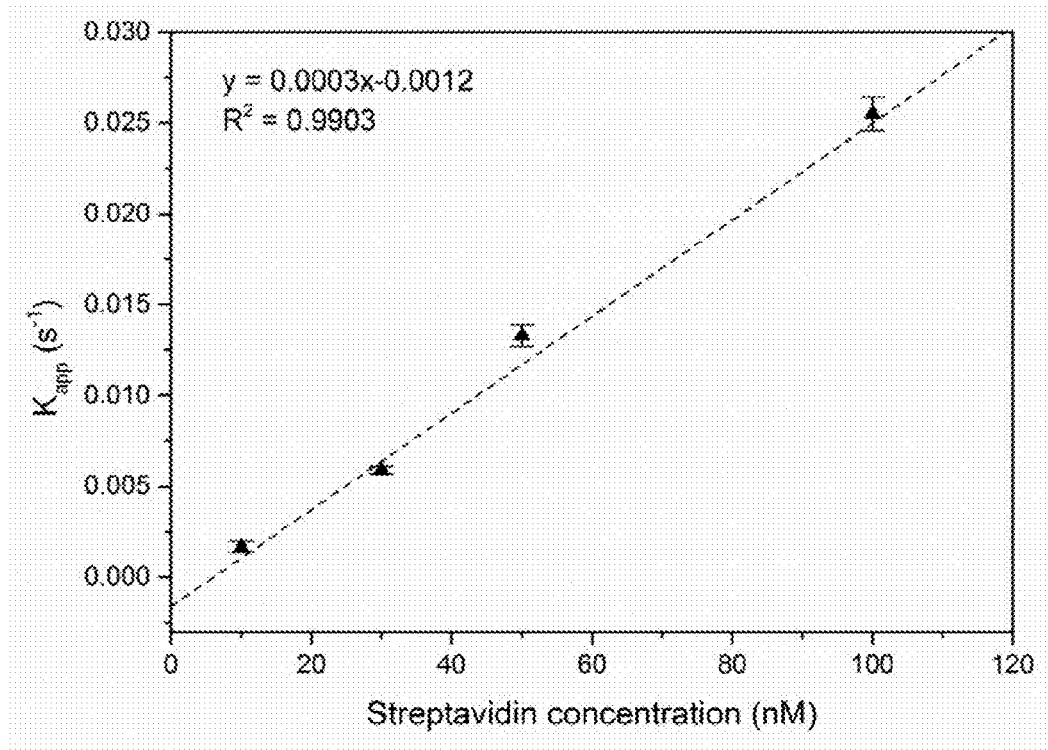
FIG. 5B is a plot of apparent rate constants ($K_{app}$) determined from non-linear least-squares fit as a function of streptavidin concentration. The plot shows linear trends with $R^2$ value of 0.9903.

The effect of various flow velocities ranging from 155-465 μm/s (associated to the $P_e$ number in the range of 0.94-2.8) on binding kinetics were also investigated however the sensor responses did not show any significant differences, indicating no mass transport limitation as expected. Therefore, the binding constant can also be determined using a simple "well-mixed" model, assuming a simple biomolecular first-order interaction. The binding of analyte to the sensor surface with an association rate constant $k_a$ and dissociation rate constant kd is given b $$C_b = \frac{k_a C_{max} C(1 - e^{(-k_a C + k_d)t})}{k_a C + k_d},$$

where C is the analyte concentration in bulk solution, $C_b$ is the bound complex concentration on the surface and $C_{max}$ is the probe density or binding sites on the surface which implies as the maximum value of $C_b$. This model is defined as "well-mixed" model assuming that the detection kinetics are reaction rate-limited and the analyte concentration is constant and uniform everywhere above the sensor surface. The apparent time constant is given by $K_{app}=k_a C+k_d$ which can be derived by fitting the kinetic curves to equation 8. A plot of apparent time constant as a function of target analyte concentration is demonstrated in FIG. 5B. It is seen that the apparent time constant increases with increasing analyte concentration. The plot gave a linear fit with a slope of 0.0003 and R-square of 0.9903. A derived slope of 0.0003 $nM^{-1}s^{-1}$ results in an association rate constant $k_a$ of $3.0 \times 10^5$ $M^{-1}s^{-1}$. This derived $k_a$ value is in a good agreement with the value extracted from our finite element model and within the reported range in the literatures based on microfluidic platform, confirming the validity of our kinetic computational model to predict the binding responses of biospecific interactions.

Model II: Mouse IgG/Anti-Mouse IgG Binding Model

To further validate our kinetic model, mouse immunoglobulin G (IgG) and anti-mouse IgG is considered as another protein-receptor pair. The diagram of surface architecture used in kinetic study for this model is described in FIG. 4B. Streptavidin-biotin bridges are widely involved in surface immobilization strategy of protein and DNA chips owning to their robustness to temperature and pH. In this study, a 10% biotinylated thiol modified surface was employed to obtain a full surface coverage of streptavidin monolayer which maximizes the exposed biotin-binding sites for additional biotinylated receptors as reported elsewhere. Generally, streptavidin molecules act as building blocks in assembling the organized monomolecular capture probe, allowing optimum anchoring of the biotinylated probe molecules with minimized non-specific adsorption of other biomolecules such as immunoglobins (IgG) or human serum albumin (HSA). This optimized surface chemistry is crucial for biosensor performances.

Figure 6A:
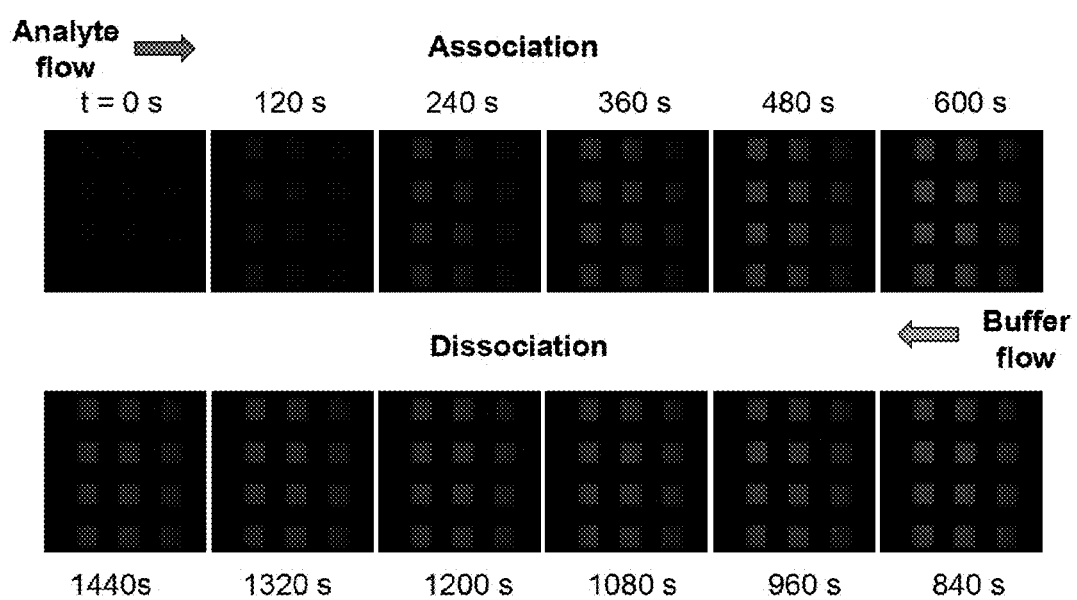
FIG. 6A is a fluorescence image snapshots taken during association and dissociation processes upon Alexa Fluor-647 mouse anti-rabbit IgG (3 nM) injection into anti-mouse modified nanoslit. The dissociation phase is achieved by simply reversing the liquid flow within the nanochannel after the end of the association phase.

After surface biotinylation, streptavidin was functionalized onto biotinylated SAM layer by introducing a 100 nM solution of ST-AF 488 at a constant flow velocity of 155 μm/s for 15 min until saturation was achieved, followed by buffer washing step. Subsequently, the sensor was subjected to biotinylated mouse anti-rabbit IgG (100 nM in PBS buffer) for 15 min and rinsed with buffer solution for 5 min. Kinetic measurements were performed by introducing various concentrations of Alexa Fluor-647 conjugated mouse anti-rabbit IgG (mIgG-AF 647) target analyte (diluted in PBS buffer) ranging from 0.46 to 15 nM to anti-mouse modified sensor chip under continuous flow velocity of 200 μm/s. The bound mouse IgG was allowed to dissociate from the surface receptor by injection of a pure buffer solution via a reversed flow manner. The fluorescence images were recorded in real-time to monitor the association and dissociation processes inside nanoslit (FIG. 6A). In this study, the association time was fixed the same for all target concentrations enabling a global analysis using BIAevaluation software package. The sensor surface was regenerated by injecting the solution of 10 mM glycine-HCl pH 2.0 for a short period of time and thoroughly rinsed with buffer solution before performing the next measurement cycle. Additionally, an irrelevant target analyte (Alexa Fluor-600 goat anti-rabbit IgG) was introduced to anti-mouse immobilized nanoslit to verify non-specific interaction however no significant increase in fluorescence intensity was observed.

Figure 6B:
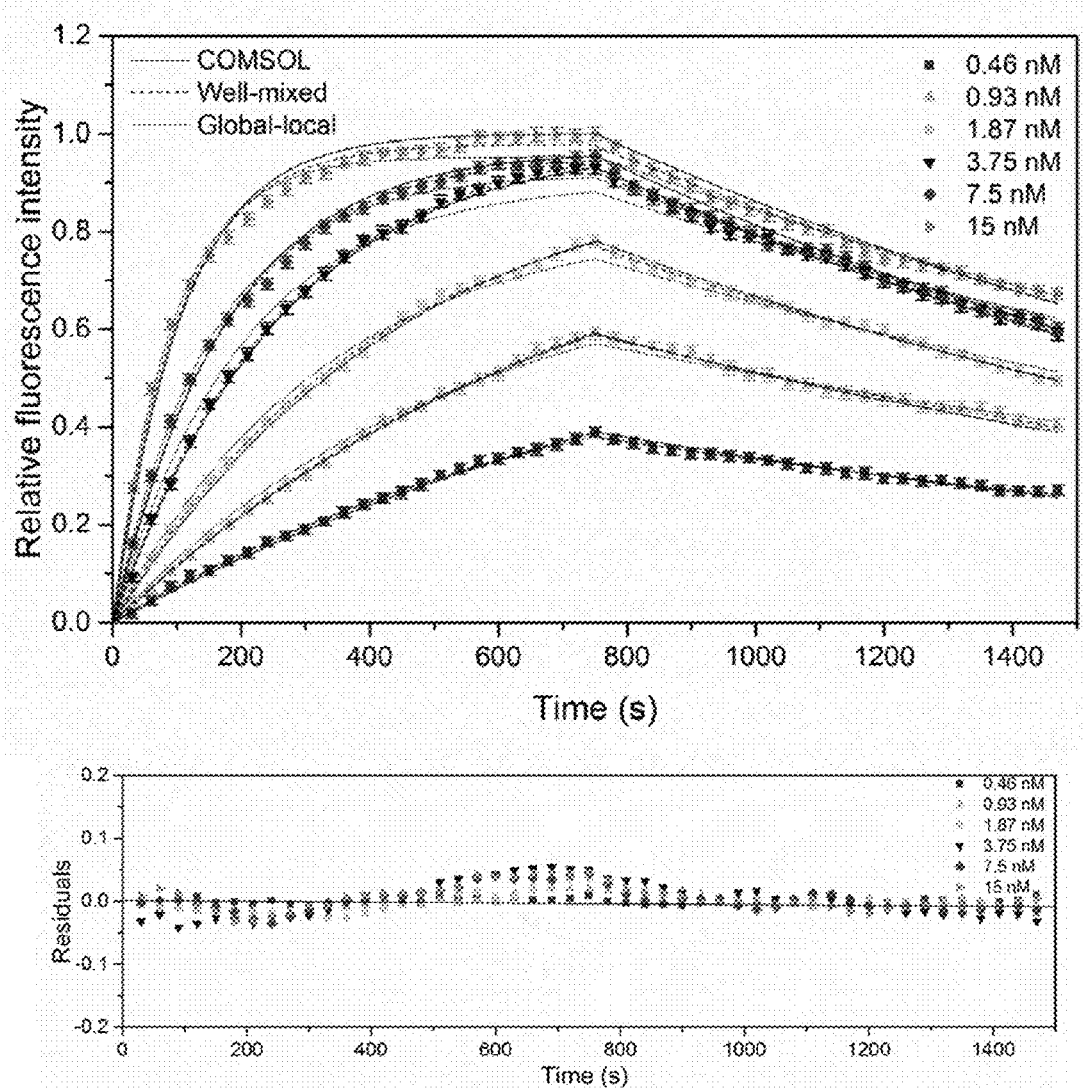
FIG. 6B shows real-time sensor responses of mouse IgG/anti-mouse IgG interaction measured in biofunctional nanoslit at various analyte concentrations ranging from 0.46 nM to 15 nM (the error bars: standard errors). The data were normalized to relative fluorescence intensity and fitted with three different models: (1) finite element simulation, (2) well-mixed model and (3) global-local fitting by BIAevaluation software package, assuming a simple Langmuir 1:1 interaction. The black (-), (- - -) and ( . . . ) lines represent the predicted curves from the best fit of finite element simulation, well-mixed model, and global-local fitting, respectively. The residual versus time plots are also demonstrated for all concentrations.
Figure 6C:
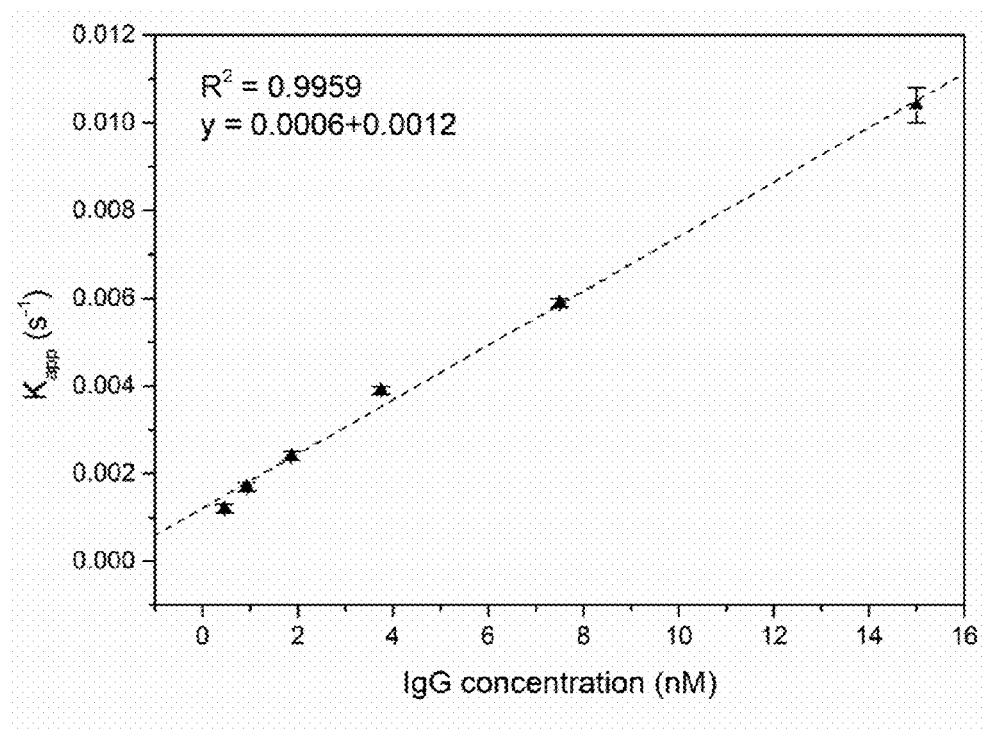
FIG. 6C shows a plot of apparent rate constants ($K_{app}$) as a function of mouse IgG concentration, showing linear trends with $R^2$ value of 0.9959.

The resulting kinetic data were then normalized and fitted with three different models: i) finite element simulation, ii) well-mixed model and iii) global-local fitting by BIAevaluation software (FIG. 6B). Based on finite element computational modeling, the binding rate constants were determined from the best fit of the predicted kinetic curves to the experimental data by means of coefficient of determination. It can be observed that our simulated kinetic model describes the immunoreaction assay in nanoslit well as each experimental binding curve was fitted accurately (R-square in a range of 0.99). The average association rate constant ($k_a$) was determined to be $8.0 \times 10^5$ $M^{-1}s^{-1}$ and dissociation rate constant ($k_d$) of $6.2 \times 10^{-4}$ $s^{-1}$ was achieved, giving an equilibrium dissociation constant $K_D$ of 0.77 nM. Furthermore, the effect of flow velocity on binding kinetics was also investigated, but the sensor responses did not show significant change, indicating no mass transport limitation. Accordingly, the experimental data were subsequently fitted to the 'well-mixed' analytical model with non-linear least squares method and the apparent time constant ($K_{app}$) was plotted as a function of analyte concentration, giving a good fit with R-square of 0.9959 (FIG. 6C). The desorption of bound analyte from the surface receptor was estimated using a first-order exponential decay. This results in the association and dissociation rate constants of $6.0 \times 10^5$ $M^{-1}s^{-1}$ and $5.5 \times 10^{-4}$ $s^{-1}$, respectively. Finally, the kinetic data were examined using a global-local analysis from BIAevaluation software. Comparable to our simulation, the best fit was found using a Langmuir 1:1 binding model. The average values of $k_a$ and $k_d$ were determined to be $12 \times 10^5$ $M^{-1}s^{-1}$ with SE of $2.0 \times 10^4$ and $5.0 \times 10^{-4}$ $s^{-1}$ with SE of $1.8 \times 10^{-5}$, respectively, supporting the validity of our finite element model for good quantitative description of the kinetic data.

Figure 6D:
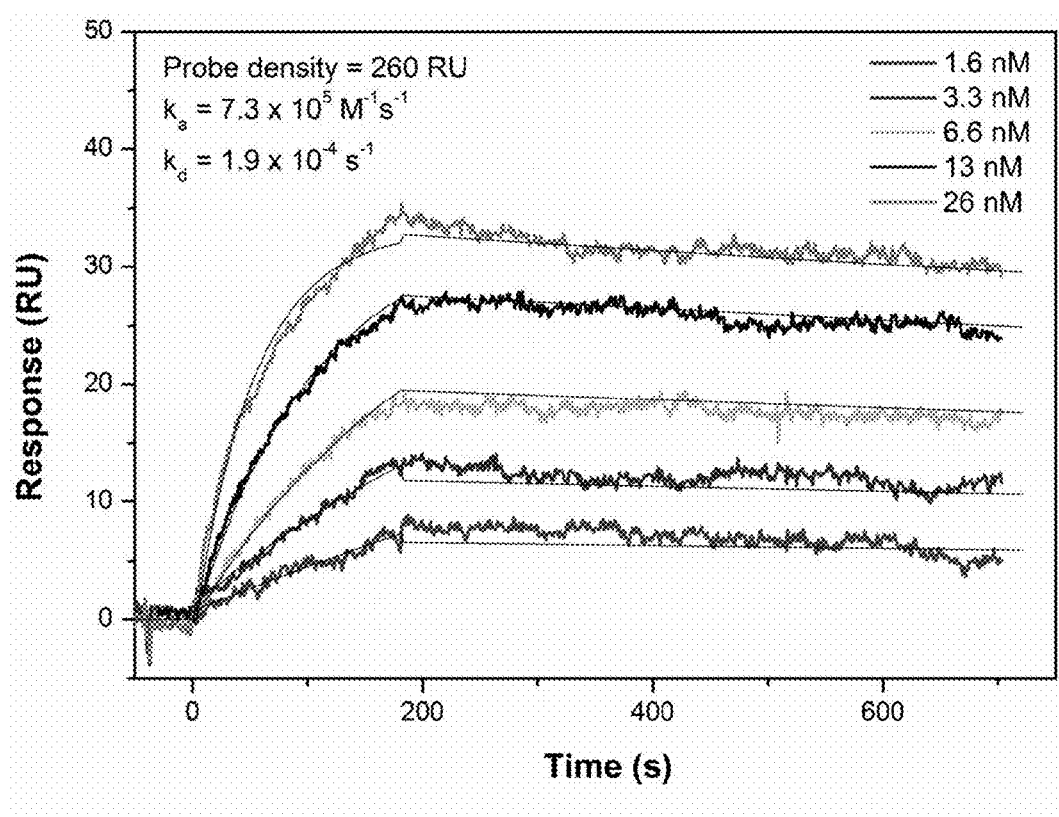
FIG. 6D shows sensorgrams of mouse IgG/anti-mouse IgG binding kinetics obtained from analogous SPR measurement. Kinetic curves were fitted using a 1:1 global analysis model from BIAevaluation software package (black line). The association and dissociation rates are found to be $7.3 \times 10^5$ $M^{-1}s^{-1}$ with SE of $3.0 \times 10^3$ and $1.9 \times 10^{-4}$ $s^{-1}$ with SE of $8.0 \times 10^{-6}$, respectively.

To further evaluate our platform, an analogous real-time kinetic measurement of mouse IgG/anti-mouse IgG was conducted using surface plasmon resonance setup. Sensorgrams containing kinetic information of these binding events at various concentrations ranging from 1.6 to 26 nM are shown in FIG. 6D. Global analysis was utilized to identify the binding model and quantify kinetic parameters using BIAevaluation software package. The best fit for the entire data was found with a 1:1 Langmuir binding model without influence of mass transport, giving $k_a$ and $k_d$ of $7.3 \times 10^5$ $M^{-1}s^{-1}$ with SE of $3.0 \times 10^3$ and $1.9 \times 10^{-4}$ $s^{-1}$ with SE of $8.0 \times 10^{-6}$, respectively. Furthermore, repeated kinetic measurements were also conducted at different immobilized surface probe densities to ensure the accuracy of determined kinetic parameters from the binding data. The estimated binding rate constants were still consistent. In summary, our nanoslit based biosensor platform yielded kinetic constants that are in a good agreement with the SPR measurement and in the range with literature values (Table 1), thus extending the validity of our model for accurately quantifying the binding kinetics of biomolecular interactions.

Table 1 Comparison of on-rate constant ($k_a$) for streptavidin-biotin binding and IgG/anti-IgG binding obtained from our biofunctional nanofluidic platform, SPR and literatures.

TABLE 1

| Binding model | Nanoslit biosensor ($\times 10^5$ $M^{-1}s^{-1}$) | | | SPR ($\times 10^5$ $M^{-1}s^{-1}$) | Literatures ($\times 10^5$ $M^{-1}s^{-1}$) |
| --- | --- | --- | --- | --- | --- |
| | FEM | Well-mixed | Global-local | | |
| Streptavidin-biotin | 7.1 | 3.0 | N/A | N/A | 4.4-450 |
| IgG/anti-mouse IgG | 8.0 | 6.0 | 12 | 7.3 | 2.5-13 |

Detection Limit Determination

Figure 7:
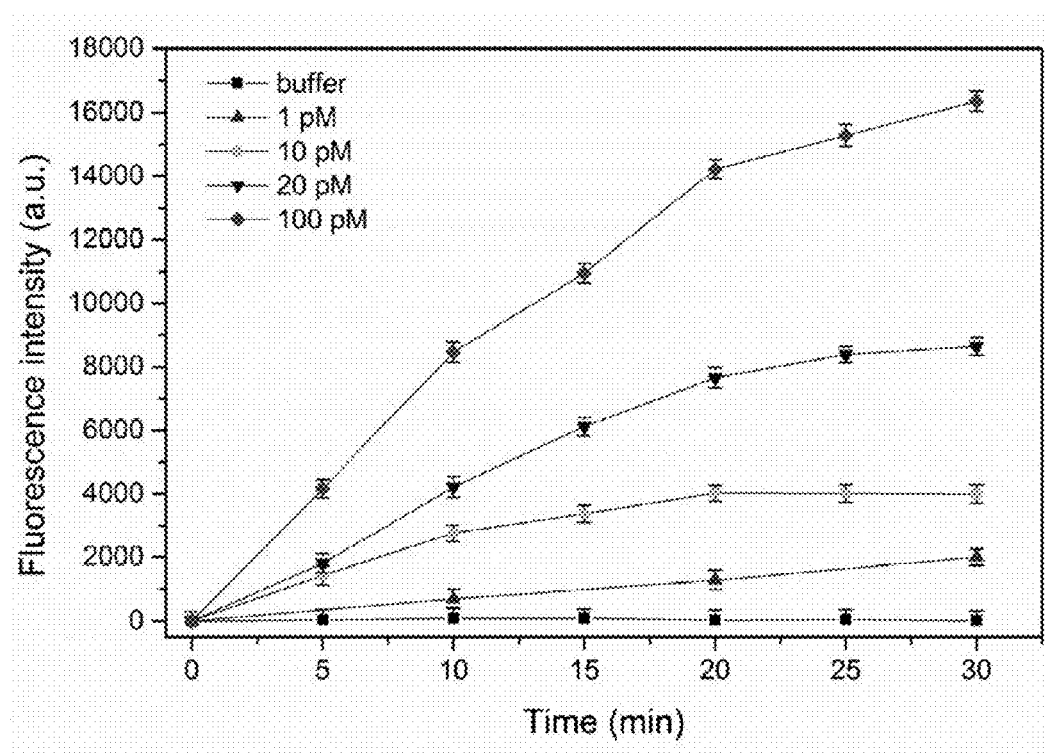
FIG. 7 shows fluorescence intensity changes with time upon the introduction of different concentrations of Alexa Fluor-647 mouse anti-rabbit IgG (mIgG-AF 647) target ranging from 0 pM (analyte-free buffer) to 100 pM on anti-mouse IgG immobilized nanoslit (the error bars: standard errors).
Figure 11:
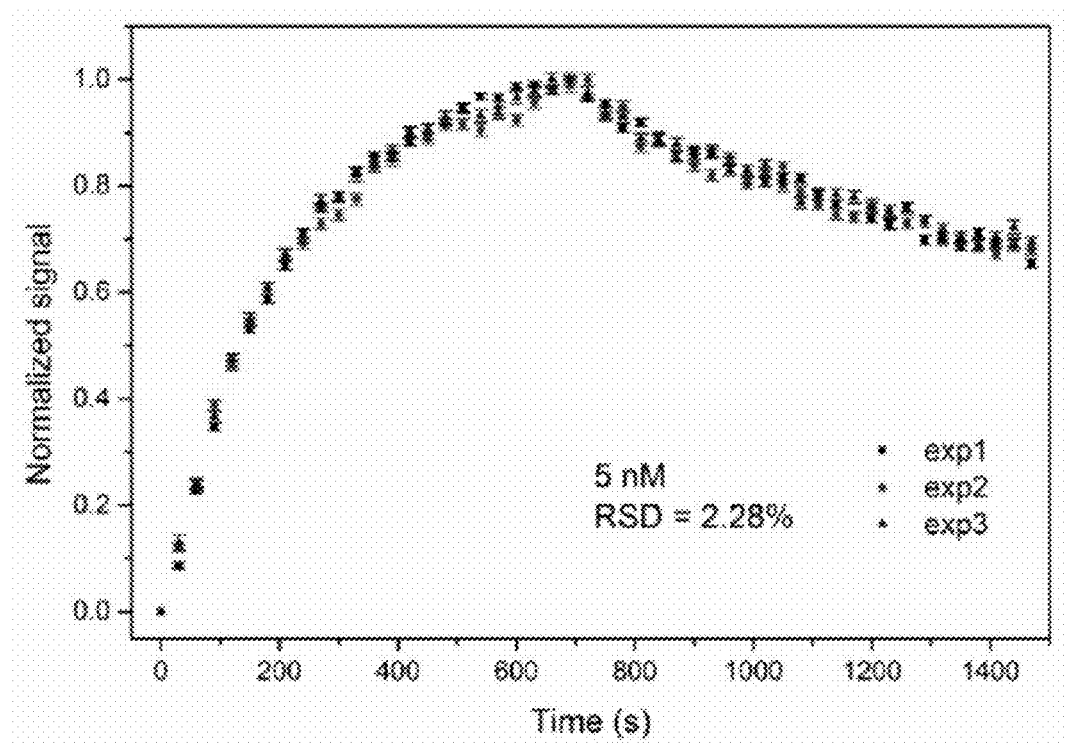
FIG. 11 shows repeatability of nanoslit biosensor for multiple detections of 5 nM Alexa Fluor-647 mouse anti-rabbit IgG (mIgG-AF 647). The plots represent the normalized fluorescence intensity as a function of time for three repeated experiments during kinetic assays on the same device (the error bars: standard errors). The data were obtained from the same area (10×10 pixels) on the gold sensor surface. The sensor was regenerated with the regeneration solution (10 mM glycine-HCl pH 2.0) and thoroughly rinsed with buffer solution before conducting the next measurement cycle. The relative standard deviation was calculated to be 2.28%.

To ensure that our device can be employed not only for investigating binding kinetics of protein-ligand interactions but can also be applied as a highly sensitive and rapid on-chip immunosensor, limit of detection (LOD) is another important performance characteristic for validation. In this study, the detection limit was determined by introducing different concentrations of mIgG-AF 647 target analyte solutions to anti-mouse IgG-modified nanoslit and the fluorescence intensity was recorded. The fluorescence intensity changes with the introduction of target analyte as a function of time are plotted in FIG. 7. No significant increase in fluorescence intensity was observed when an analyte-free buffer solution was injected, while introduction of 1 pM resulted in a significant increase in fluorescence intensity after 30 min (S/N~3). With a sample volume of 10.5 nL, a mole detection limit can be determined as 10 zeptomole. Notably, increasing the analyte concentration to 10 pM, our sensor can easily detect the binding response signal within 5 min. The value of detection limit obtained from our system for mouse IgG sensing is significantly better than or comparable to existing microfluidic immunosensing formats. Additionally, this on-chip immunosensor shows good repeatability with a standard deviation of 2.28% at analyte concentration of 5 nM (FIG. 11). Furthermore, the total immunoassay time (including injection, immobilization and detection steps) required for mouse IgG detection based on streptavidin-biotin linkage for anti-mouse IgG immobilization was found to be approximately 40 min in our study while the traditional enzyme-linked immunosorbent assay (ELISA) takes hours to days to complete the whole assay. Therefore, our approach also demonstrates fast and sensitive immunosensing platform for protein detection with low reagent consumption, indicating a great potential in clinical diagnosis.

The present invention provides a sensing device and a sensing method which are practically a biofunctionalized nanofluidic slits applied with classical fluorescence microscopy techniques, providing a simple, low-cost but still effective biosensing platform for kinetics studies. The sensing device includes a channel which depth is reduced to the sub-micrometer range, thus providing the following advantages of the present invention: (1) The drastic reduction of the diffusion length permits to operate in a reaction-limited regime with optimized target capture efficiency. Hence, all analyte molecules injected in the device are analyzed, and the dissociation study can be simply implemented after completion of the association phase by reserving the fluid flow within the channel instead of injecting new buffer in the inlet, which results in a simplified operating protocol and reduced time of analysis; (2) a sampling volume reduction allows the device directly probing the sensing surface with conventional fluorescence microscopes without the need of using complicated and expensive setups, such as SPR, TIRFM, or QCM; (3) the signal to noise ratio is inversely proportional to the channel height: sub-micrometer channels thus offers signal to noise ratio of at least 100 on a large scale of dissociation constant $K_D$, from the pM to the sub-μM range, that concerns most molecules of interests.

Moreover, the sensing device and the sensing method of the present invention enables large sampling area over a number of pixels ensuring much reduced statistical errors (higher precision) than non-spatially resolved sensing platforms. More importantly, Fluorescence microscopy offers a limit of detection under the pM with no effect of analyte mass, thus allowing the sensing device and the sensing method of very high-affinity interactions and small molecules.

The present invention solves the prior art problems by providing: (1) shortened kinetic assay time due to the reversed flow operation while higher level of detection sensitivity can be achieved with a very simple set-up, (2) efficient target capture for minute sample analysis, and (3) spatiotemporally resolved reaction/binding kinetics allowing for low statistical error.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A sensing device applied to an analyte molecule of a liquid sample and a buffer flow, comprising:
   at least one first inlet, for inputting the liquid sample;
   at least one second inlet, for inputting the buffer flow;
   a micro-flow channel, communicating with the first inlet and the second inlet; and at least one immobilization element for immobilizing a sensing molecule for the analyte molecule and the buffer flow in the micro-flow channel, wherein the micro-flow channel has two ends which are respectively connected to the first inlet and the second inlet, and the micro-flow channel is between the first inlet and the second inlet, wherein the sensing molecule is capable of generating an association reaction with the analyte molecule of the liquid sample, and generating a dissociation reaction with the analyte molecule and the buffer flow in reverse direction, wherein the sensing molecule and the analyte molecule of the liquid sample are configured to generate the association reaction after the liquid sample flows into the micro-flow channel for association reaction observation, and then the sensing molecule and the analyte molecule are configured to generate the dissociation reaction after the buffer flow flows reversely into the micro-flow channel for dissociation reaction observation.

2. The device of claim 1, wherein the micro-flow channel has an enough length so that the association reaction of the sensing molecule and the analyte molecule is observable.

3. The device of claim 1, wherein the association reaction of the sensing molecule and the analyte molecule exhibits fluorescence.

4. The device of claim 1, further comprising:
a substrate, having a plurality of grooves corresponding to the first inlet, the second inlet and the micro-flow channel; and
a cover, facing the grooves and combined with the substrate, wherein the cover and the grooves forms the first inlet, the second inlet and the micro-flow channel,
wherein the immobilization element is disposed on the groove corresponding to the micro-flow channel.

5. The device of claim 4, wherein the material of the substrate comprises silicon, silicon dioxide, glass, and/or plastics, the material of the cover comprises polydimethylsiloxane, hard polydimethylsiloxane, polysilsesquioxane (PSQ), and/or plastics in bare form or coated on a glass slide, and the immobilization element is formed by surface treatment on the substrate with gold patch, glass or plastics.

6. The device of claim 4, wherein the liquid sample flows along a first direction extending from the first inlet to the second inlet, and the range of the length of the micro-flow channel between the first inlet and the second inlet is between 100 µm~5 cm, the range of the average distance between the substrate and the cover is between 50 nm~10 µm, and the range of the length of the immobilization element on the first direction is between 1 µm to the whole micro-flow channel length.

7. The device of claim 1, further comprising:
a container, communicating with the second inlet for storing the buffer flow.

8. The device of claim 1, wherein the micro-flow channel comprises a plurality of nanoslits.

9. A sensing system, comprising:
a device as in claim 1;
a flow generator, connecting to the first inlet and the second inlet;
a flow control unit, configured to control the flow generator to generate flow from the first inlet to the second inlet so as to drive the liquid sample to flow from the first inlet through one end of the micro-flow channel into the micro-flow channel for association reaction observation, and to drive the buffer flow from the second inlet through the other end of the micro-flow channel to flow reversely into the micro-flow channel for dissociation reaction observation;
a capture unit, capturing at least one image from the micro-flow channel; and
a computing unit, generating a sensing result according to the image.

10. The sensing system of claim 9, wherein the flow generator includes one or more of the following: pressure pump or capillarity pump for pressure-driven flow, thermal gradient induced flow, or electrokinetic pump for electroosmotic flow.

11. The sensing system of claim 9, wherein the capture unit captures first time-lapse images from the micro-flow channel for association reaction and captures second time-lapse images from the micro-flow channel for disassociation reaction, and the computing unit utilizes association kinetics and dissociation kinetics to generate the sensing result according to the first time-lapse images and the second time-lapse images.

12. A sensing method applied to the device as in claim 1, comprising:
driving the liquid sample into the micro-flow channel from the first inlet through one end of the micro-flow channel so as to associate the analyte molecule of the liquid sample with the sensing molecule for association reaction observation;
driving the buffer flow reversely into the micro-flow channel from the second inlet through the other end of the micro-flow channel so as to disassociate the analyte molecule from the sensing molecule for dissociation reaction observation; and
generating a sensing result as a sensorgram, according to the associating result and the disassociating result.

13. The sensing method of claim 12, wherein the generating step further comprises:
obtaining an association kinetics information according to the associating result;
obtaining a disassociation kinetics information according to the disassociating result; and
obtaining the sensing result according to the association kinetics information and the disassociation kinetics information.

14. The sensing method of claim 12, wherein the generating step further comprises:
analyzing a fluorescence intensity from the associating result to obtain an association kinetics information;
analyzing another fluorescence intensity from the disassociating result to obtain a disassociation kinetics information;
obtaining the sensing result according to the association kinetics information and the disassociation kinetics information.

15. The sensing method according to claim 12, further comprising:
driving a regenerating solution into the micro-flow channel;
rinsing the micro-flow channel with the regenerating solution; and
removing the regeneration solution from the micro-flow channel.

* * * * *